(12) United States Patent
Wurzberger

(10) Patent No.: US 8,273,384 B2
(45) Date of Patent: Sep. 25, 2012

(54) PROCESS FOR THE PREPARATION OF A NON-CORROSIVE BASE SOLUTION AND METHODS OF USING SAME

(76) Inventor: Stephen Ray Wurzberger, Goodyears Bar, CA (US)

( * ) Notice: Subject to any disclaimer, the term of this patent is extended or adjusted under 35 U.S.C. 154(b) by 1023 days.

(21) Appl. No.: 12/167,123

(22) Filed: Jul. 2, 2008

(65) Prior Publication Data

US 2009/0047267 A1 Feb. 19, 2009

(51) Int. Cl.
*A61K 33/08* (2006.01)
*A61K 33/04* (2006.01)
*A01N 59/02* (2006.01)
*A01N 59/06* (2006.01)

(52) U.S. Cl. .................... 424/693; 424/709; 423/581

(58) Field of Classification Search .................... None
See application file for complete search history.

(56) References Cited

U.S. PATENT DOCUMENTS 5,571,336 A * 11/1996 Wurzburger et al. ............. 134/2
2007/0149623 A1 6/2007 Godin

OTHER PUBLICATIONS

Harrison's Principles of Internal Medicine, (13th Edition, Harrison et al, Ed.s, 1994, p. 258).*

Azzi et al (FEBS Letters, 2004, vol. 558, pp. 3-6).*

* cited by examiner

*Primary Examiner* — Karen Canella
(74) *Attorney, Agent, or Firm* — Jeffrey J. King; Patent Networks Law Group PLLC

(57) ABSTRACT

The present invention provides novel methods of making a non-corrosive base solution for use as an alkalinity increasing agent and/or antioxidant. The present invention further provides novel compositions and methods which can be used to provide relief from disorders related to or complicated by acidosis or excessive free radical or other reactive oxygen species production including, but not limited to, gout, Lesch-Nyhan syndrome, hemochromatosis, Alzheimer's, amyotropic lateral sclerosis, arthritis, atherosclerosis, cancer, cataracts, chronic obstructive pulmonary disease, diabetes, cellulitis, coronary artery disease, heart failure, hypertension, inflammatory bowel disease, macular degeneration, multiple sclerosis, Parkinson's, Reynaud's phenomenon, reperfusion injury, pancreatic impairment, skin infections, Hepatitis C, methicillin-resistant *Staphylococcus aureus* and infection. The compositions and methods of the present invention additionally supply relief from microbial infections including fungal infections as well as prevent secondary infections. Additional compositions and methods are provided which employ a non-corrosive base solution in combination with a second alkalinity increasing agent and/or antioxidant, or other therapeutic agent to yield a more effective treatment tool against acidosis and/or excessive ROS production including free radical production useful to prevent or reduce acidosis and/or excessive ROS production or related symptoms or conditions associated with acidosis and/or excessive free radical production in mammalian subjects.

15 Claims, No Drawings

PROCESS FOR THE PREPARATION OF A NON-CORROSIVE BASE SOLUTION AND METHODS OF USING SAME

TECHNICAL FIELD

The present invention relates to methods of making a non-corrosive base solution and the use of the non-corrosive base solution. More specifically, the present invention relates to methods and compositions for altering physiological pH and reducing reactive oxygen species in mammals.

BACKGROUND

The pH, or hydrogen ion concentration, [H+], of natural environments varies from about 0.5 in the most acidic soils to about 10.5 in the most alkaline lakes. The range of pH over which an organism grows is defined by the minimum pH, below which the organism cannot grow or reproduce; the maximum pH, above which the organism cannot grow or reproduce; and the optimum pH, at which the organism grows best. For most organisms there is an orderly increase in growth rate and reproduction rate between the minimum and the optimum pH and a corresponding orderly decrease in growth rate and reproduction rate between the optimum and the maximum pH, reflecting the general effect of changing [H+] on the rates of enzymatic reaction.

The pH of interstitial and intracellular fluids in mammals is one of the physiologic barriers that contribute to innate immunity. For example, gastric acidity provides an innate physiologic barrier to infection because very few ingested microorganisms can survive the low pH of the stomach. Hair follicles secrete sebum that contains lactic acid and fatty acids both of which inhibit the growth of some pathogenic bacteria and fungi.

In contrast to the acidity of gastric acid and sebum, blood and lymph are both slightly alkaline with the optimal pH of blood maintained between a pH 7.3 to 7.4 and the pH of lymph at about 7.5. An alteration in the normal pH of any of these fluids may make an individual more susceptible to infection and disease by creating a more hospitable environment for microorganisms to grow.

The pH of the human body is maintained through the actions of buffers, respiration, and renal function. In dealing with the normal acid load from diet and metabolism, buffers such as proteins, phosphate and $H_2CO_3:HCO_3^-$ act to control the pH level. Respiration maintains a constant carbonic acid level at 1.2 meq/l or $PaCO_2$ of 40 mmHG through either excretion or retention of $CO_2$ by the lungs. Respiration can also rapidly compensate for changes in pH by altering the level of $PaCO_2$ through the alteration of alveolar ventilation. The renal system manipulates the volume and composition of extracellular fluid to help maintain the pH of plasma. However, while the renal system can correct states of excess, it cannot correct states of deficiency such as through loss of Na+, K+ or $HCO_3^-$. Unlike respiratory regulation, regulation of pH through renal function can take several days.

A natural byproduct of the normal metabolism of oxygen is reactive oxygen species (ROS). ROS are generally very small molecules such as free radicals, oxygen ions and peroxides that are highly reactive due to the presence of unpaired valence shell electrons. While these molecules play an important roll in cell signaling, during times of environmental stress ROS levels can increase dramatically resulting in significant damage to cell structures. ROS have been implicated in aging, cancer, cardiovascular disease as well as other kinds of cellular damage to the body.

Cells normally protect themselves from reactive oxygen species through free radical scavengers and chain reaction terminators including enzymes such as superoxide dismutase (SOD), catalase, and the glutathione peroxidase system as well as other antioxidants; however, antioxidant supply is non-catalytic in nature and one antioxidant molecule can only react with a single free radical. Therefore, there is a constant need to replenish antioxidant resources, whether endogenously or through supplementation.

Failure or overloading of any one of these regulatory mechanisms, whether through stress, pharmacological treatments, diet, infection, lactic acidosis, and other diseases and conditions, including but not limited to, cancer, cardiovascular disease, metabolic diseases and disorders, diabetes, cellulitis and pancreatic impairment. There is therefore a need for compositions that can compensate for the failure of regulatory mechanisms to regulate physiological pH and prevent acidosis as well as reduce levels of reactive oxygen species.

SUMMARY OF THE EXEMPLARY EMBODIMENTS OF THE INVENTION

In one embodiment, the present invention is directed to methods and compositions for modifying physiological pH.

In a further embodiment, the present invention provides a non-corrosive base solution for vertebrate consumption including consumption by mammals such as humans.

In an additional embodiment, the present invention provides a method for increasing the solubility of calcium hydroxide in solution.

In another embodiment, the present invention provides a novel anti-microbial.

In an additional embodiment, the present invention is directed to methods and compositions for preventing and treating acidosis.

In a further embodiment, the present invention is directed to methods and compositions for treating conditions associated with acidosis.

In yet another embodiment, the present invention is directed to methods and compositions for providing antioxidants.

In still another embodiment, the present invention provides compositions and methods for regulating free radical levels.

In a further embodiment, the present invention provides compositions and methods for regulating reactive oxygen species (ROS).

In yet another embodiment, the present invention provides compositions and methods for preventing secondary infections in mammalian subjects with compromised immune systems.

In a further embodiment, the present invention provides compositions and methods for neutralizing acids.

In still another embodiment, the present invention is directed to methods and compositions for optimizing the effectiveness of other pharmaceutical agents.

In yet another embodiment, the present invention is directed to methods and compositions for neutralizing stomach acid in vertebrates, including mammals.

The normal pH of intracellular and interstitial fluids is maintained because acids are removed at the same rate they are added. If acid is added faster than it is removed, the pH of intracellular and interstitial fluids decreases, resulting in acidosis. While strong mineral bases have often been used to neutralize acids, they are very corrosive and are not generally suitable for altering pH in living organisms. The present invention provides compositions and methods for altering base solutions so that they may be effectively used to increase pH in living organisms.

Reactive oxygen species including free radicals are produced as part of the normal metabolic process. They are generally prevented from causing damage through enzymes such as superoxide dismutases and catalases as well as antioxidants or other free radical scavengers. When levels of ROS exceed the neutralizing capacity of the body's regulatory mechanisms, such as during periods of intense exercise or due to a failure in endogenous antioxidant production, cellular damage, mutation and/or mortality levels increase. Proton absorbers which have previously been used to reduce free radicals are not true bases and require consumption of such large amounts that they are not generally suitable for prolonged use.

The methods and formulations of the present invention provide a base solution with a high concentration of $OH^-$ ions which may be used as an alkalinity increasing agent and/or an antioxidant or free radical scavenger. In some embodiments, the methods of the present invention combine a magnetically treated calcium hydroxide solution with an ozone treated sulfuric acid solution to create such a base solution with a high concentration of $OH^-$ ions.

Calcium hydroxide ($Ca(OH)_2$) is a base which may be used as an acid neutralizing agent and/or antioxidant. However, it will only dissociate slightly in a weak acid environment. At a pH of 5.5 or higher, calcium hydroxide rapidly loses its solubility and at a pH of 8.0 it is insoluble. In one embodiment, the present invention provides a method of increasing the solubility of calcium hydroxide allowing a larger volume of $Ca(OH)_2$ to be dissociated in solution including weakly acidic, neutral or slightly basic solutions. In a further embodiment, the present invention provides a means of raising the pH of a $Ca(OH)_2$ solution at least one pH point higher than a normal saturated calcium hydroxide solution. In some embodiments, the present invention provides a method of increasing the reactivity of $Ca(OH)_2$ in solution. In another embodiment, the present invention provides a method for increasing the level of free hydroxide in a solution made with $Ca(OH)_2$ through the removal of calcium ions.

Useful forms of calcium hydroxide for use within the formulations and methods of the invention include the forms described herein, as well as solvates, hydrates, or combinations thereof.

Sulfuric acid is a strong mineral acid. In the compositions and methods of the present invention, sulfuric acid in water is treated to reduce the acidity while maintaining the concentration of sulfate in the solution. Such treatment may be accomplished by any means possible, including the addition of oxygen to the sulfuric acid solution. In some embodiments, the sulfuric acid solution is infused with ozone. Such treatments may increase the pH of the sulfuric acid solution, creating a neutral or basic solution which may then be combined with the calcium hydroxide solution described above to create a non-corrosive base solution with a high concentration of $OH^-$ ions.

In exemplary embodiments, the compositions and methods of the invention employ a base solution (also referred to as an $OH^-$ solution or alkaline water) made from calcium hydroxide to increase physiological pH. Mammalian subjects amenable for treatment according to the formulations and methods of the invention include, but are not limited to, human and other mammalian subjects with acidosis, as well as conditions associated with or complicated by acidosis including cancer, cardiovascular disease, respiratory disease, infection, diabetes, cellulitis and pancreatic impairment.

These and other subjects are effectively treated prophylactically and/or therapeutically by administering to the subject an effective amount of a base solution prepared using calcium hydroxide. As noted above, the methods and formulations of the present invention may employ calcium hydroxide in a variety of forms including solvates, hydrates, or combinations thereof in forming the base solution.

Within additional aspects of the invention, a composition made using the base solution and additional alkalinity increasing agents may be combinatorially formulated or coordinately administered to yield an effective alkalizing treatment. The compositions and methods of the present invention provide certain advantages in regulating pH in a mammalian subject. The combination of a composition made using calcium hydroxide or a solvate, or hydrate thereof and an additional alkalinity increasing agent will yield an enhanced therapeutic response beyond the therapeutic response elicited by either agent alone.

Useful secondary or additional alkalinity increasing agents for use within the formulations and methods of the present invention include sodium bicarbonate; a carbonate, a phosphate, or a hydroxide of sodium or potassium; magnesium carbonate; magnesium hydroxide; ammonium carbonate; ammonium bicarbonate; magnesium oxide; sodium or potassium citrate, bicarbonate, sulfate, and benzoate; ascorbate; calcium carbonate; any pharmaceutically acceptable material that causes the pH of an aqueous medium to rise above pH 7.0, or mixtures thereof.

In some embodiments, the alkalizing treatment may be administered in combination with therapeutic agents other than additional alkalinity increasing agents. Such combinations may increase the effectiveness of therapeutic agents used to treat particular diseases or conditions such as cancer. In further embodiments, such combinations may decrease the required effective amount of the other therapeutic agents. In some embodiments, the alkalizing treatment may facilitate the administration of therapeutic agents or organic substances which are vulnerable to acidic conditions such as those found in the stomach.

The compositions of the present invention are further effective in preventing secondary infections in mammalian subjects with compromised immune systems, such as those subjects suffering from chronic diseases such as cancer or HIV.

In additional exemplary embodiments, the compositions and methods of the invention employ an $OH^-$ composition made from calcium hydroxide as an antioxidant and free radical scavenger, providing certain advantages in regulating free radical and other ROS levels in a mammalian subject.

Mammalian subjects amenable for treatment according to the formulations and methods of the invention further include, but are not limited to, human and other mammalian subjects in need of antioxidant treatment or ROS reduction or management, including those suffering from conditions associated with or complicated with excess free radicals such as gout, Lesch-Nyhan syndrome, hemochromatosis, Alzheimer's, amyotrophic lateral sclerosis, arthritis, atherosclerosis, cancer, cataracts, chronic obstructive pulmonary disease, diabetes, coronary artery disease, heart failure, hypertension, inflammatory bowel disease, macular degeneration, multiple sclerosis, Parkinson's, Reynaud's phenomenon, cellulitis, methicillin-resistant *Staphylococcus aureus*, hepatitis C and reperfusion injury. In addition, the compositions of the present invention have proven effective in the treatment of skin conditions such as psoriasis, Morgellons disease, and fungal infections including but not limited to candidiasis, tinea cruris, and tinea pedis.

These and other subjects are effectively treated prophylactically and/or therapeutically by administering to the subject a free radical reducing effective amount (antioxidant effective amount) of an OH⁻ solution made from calcium hydroxide of the present invention alone or in combination with a secondary antioxidant agent or additional therapeutic agent. As noted above, the methods and formulations of the present invention may employ calcium hydroxide in making the OH⁻ solution and/or an additional antioxidant agent in a variety of forms including solvates, hydrates, or combinations thereof.

Useful secondary or additional antioxidants for use within the formulations and methods of the present invention include, but are not limited to, xanthine oxidase inhibitors including, but not limited to, allopurinol and folic acid; NADPH oxidase inhibitors, including, but not limited to, adenosine; calcium channel blockers; superoxide dismutases; catalases; albumin; inhibitors of iron redox cycling, including, but not limited to deferoxamine, apotransferin and ceruloplasmin; beta carotene; ascorbates; myricetin-3-O-galactoside, quercitin-3-O-galactoside; and alpha tocopherol.

Additional therapeutic agents for use within the formulations and methods of the present invention include, but are not limited to, therapeutic agents generally used to treat gout, Lesch-Nyhan syndrome, hemochromatosis, Alzheimer's, amyotrophic lateral sclerosis, arthritis, atherosclerosis, cancer, cataracts, chronic obstructive pulmonary disease, diabetes, coronary artery disease, heart failure, hypertension, inflammatory bowel disease, macular degeneration, multiple sclerosis, Parkinson's, Reynaud's phenomenon, cellulitis, methicillin-resistant *Staphylococcus aureus*, hepatitis C, reperfusion injury, psoriasis, Morgellons disease, and fungal infections including but not limited to candidiasis, tinea cruris, and tinea pedis.

The foregoing and other objects, features, aspects and advantages of the present invention will become more apparent from the following detailed description of the invention and examples, which are intended to exemplify non-limiting embodiments of the invention.

DETAILED DESCRIPTION OF EXEMPLARY EMBODIMENTS OF THE INVENTION

The present invention provides novel methods for making a non-corrosive strong base solution (also referred to as an OH⁻ solution, a base solution or alkaline water) and methods for using the solution for the regulation of physiological pH in vertebrates, including mammals. Increasing physiological pH is effective in the treatment of disease, including but not limited to, microbial infections, including bacterial, viral and fungal infections; cellular damage due to byproducts of cancer; treatment of respiratory disease; treatment of renal disease; treatment of pancreatic impairment; and treatment of diabetes.

The present invention additionally provides methods of using the non-corrosive strong base solution (also referred to as an OH⁻ solution, a base solution or alkaline water) as an antioxidant. Antioxidants may be used in the reduction of reactive oxygen species in vertebrates, including mammals. Reduction of free radicals and other reactive oxygen species (ROS) is effective in the treatment of diseases including, but not limited to, gout, Lesch-Nyhan syndrome, hemochromatosis, Alzheimer's, amyotrophic lateral sclerosis, arthritis, atherosclerosis, cancer, cataracts, chronic gout, chronic obstructive pulmonary disease, diabetes, coronary artery disease, heart failure, hypertension, inflammatory bowel disease, macular degeneration, multiple sclerosis, Parkinson's, Reynaud's phenomenon, cellulitis, methicillin-resistant *Staphylococcus aureus*, hepatitis C and reperfusion injury.

Another embodiment of the present invention provides methods for treating skin conditions in vertebrates, including mammals, including conditions such as, but not limited to, psoriasis, Morgellons disease and fungal infections including but not limited to candidiasis, tinea cruris, and tinea pedis.

A further embodiment of the present invention provides a strong base solution (also referred to as an OH⁻ solution, a base solution or alkaline water) for use in the prevention of secondary infections in vertebrates, including mammalian subjects; particularly mammalian subjects with compromised immune systems, such as those subjects suffering from chronic diseases such as, but not limited to, cancer or HIV, or whose immune systems are compromised due to treatments for diseases such as cancer.

An additional embodiment of the present invention provides methods of using the strong base solution to increase the effectiveness of other pharmaceutical agents.

For the purposes of describing the present invention, the following terms and definitions are provided by way of example. Additional terms and definitions for describing embodiments of the present invention are provided by way of example elsewhere in the application.

As used herein, "microbial" refers to any microorganism capable of causing disease. Such microorganisms include fungal, viral and bacterial microorganisms.

By the term "effective amount" of a compound is meant a non-toxic but sufficient amount of the compound to provide the desired function, i.e., anti-infective, as an antioxidant, or acid-neutralizing agent. An appropriate effective amount may be determined by one of ordinary skill in the art using only routine experimentation.

Formulations and methods herein employ an OH⁻ solution made from calcium hydroxide alone or with an additional alkalinity increasing agent for the regulation of physiological pH. Within these formulations and methods, the secondary alkalinity increasing agent may be provided in any of a variety of forms, including any polymorphs, enantiomers, pharmaceutically acceptable salts, solvates, hydrates, or combinations thereof. Such combinations of an OH⁻ composition and secondary alkalinity increasing agent may be administered either combinatorially or coordinately as disclosed herein to effectively treat mammalian subjects with acidosis as well as complications associated with acidosis such as increased infection, cancer, diabetes and pancreatic impairment.

Alkalinity increasing agents for use within the formulations and methods of the present invention include, but are not limited to sodium bicarbonate; a carbonate, a phosphate, or a hydroxide of sodium or potassium; magnesium carbonate; magnesium hydroxide; ammonium carbonate; ammonium bicarbonate; magnesium oxide; sodium or potassium citrate, bicarbonate, sulfate, and benzoate; ascorbate; calcium carbonate; any pharmaceutically acceptable material that causes the pH of an aqueous medium to rise above pH 7.0, or mixtures thereof.

Formulations and methods herein may additionally employ a base solution as an antioxidant or free radical scavenger for the regulation of ROS levels including free radical levels. Within these formulations and methods, the calcium hydroxide used to produce the OH⁻ solution may be provided in any of a variety of forms, including solvates, hydrates, or combinations thereof. Formulations containing a non-corrosive strong base solution made from calcium hydroxide as disclosed herein are effectively used to treat mammalian subjects suffering from an over accumulation of free radicals as well as diseases and conditions associated with free radicals including, but not limited to gout, Lesch-Nyhan syndrome, hemochromatosis, Alzheimer's, amyotrophic lateral sclerosis, arthritis, atherosclerosis, cancer, cataracts, chronic obstructive pulmonary disease, diabetes, coronary artery disease, heart failure, hypertension, inflammatory bowel disease, macular degeneration, multiple sclerosis, Parkinson's, Reynaud's phenomenon, hepatitis C, cellulitis, methicillin-resistant *Staphylococcus aureus*, reperfusion injury, and skin conditions including, but not limited to, psoriasis, Morgellons disease, candidiasis, tinea cruris, and tinea pedis.

Formulations and methods herein may also employ an $OH^-$ composition made from calcium hydroxide alone or with an additional antioxidant agent as an antioxidant or free radical scavenger. Within the methods and compositions of the invention, a base solution alone or in combination with a second antioxidant agent or their derivatives are effectively formulated or administered as an antioxidant.

Antioxidants for use within the formulations and methods of the present invention include, but are not limited to, xanthine oxidase inhibitors including, but not limited to allopurinol and folic acid; NADPH oxidase inhibitors, including, but not limited to, adenosine; calcium channel blockers; superoxide dismutases; catalases; albumin; inhibitors of iron redox cycling, including, but not limited to deferoxamine, apotransferin and ceruloplasmin; beta carotene; ascorbates; myricetin-3-O-galactoside, quercitin-3-O-galactoside; and alpha tocopherol.

A broad range of mammalian subjects, including human subjects, are amenable for treatment using the formulations and methods of the invention. These subjects include, but are not limited to, human and other mammalian subjects with acidosis and/or excessive free radical production as well as those suffering from conditions or complications of having acidosis including increased susceptibility to microbial infections or other secondary infections; skin infections such as, but not limited to, psoriasis, Morgellons disease, and fungal infections such as candidiasis, tinea cruris, and tinea pedis; cancer; diabetes; cellulitis; or pancreatic impairment; and/or mammals in need of antioxidant treatment or free radical elimination, including those suffering from conditions or complications associated with excess free radicals, including, but not limited to, gout, Lesch-Nyhan syndrome, hemochromatosis, Alzheimer's, amyotrophic lateral sclerosis, arthritis, atherosclerosis, cancer, cataracts, chronic obstructive pulmonary disease, diabetes, cellulitis, coronary artery disease, heart failure, hypertension, inflammatory bowel disease, macular degeneration, multiple sclerosis, Parkinson's, Reynaud's phenomenon, methicillin-resistant *Staphylococcus aureus*, hepatitis C, reperfusion injury and infection.

The $OH^-$ solution of the present invention may be formed through the dissolution of calcium hydroxide in water. In some embodiments, the calcium may be between 2 and 10% mole weight, preferably between 2 and 6% mole weight, more preferably 4% mole weight in water. Dissociation of the calcium hydroxide in water may be facilitated by any means applicable. In some embodiments, the calcium hydroxide solution may be agitated. In other embodiments, the calcium hydroxide solution may be exposed to a magnetic field. In further embodiments, the calcium hydroxide solution may be agitated while being exposed to a magnetic field.

Such manipulation of the solution will yield substantial dissolution of the calcium hydroxide, creating a supersaturated solution. In some embodiments, substantial dissolution is such that the dissociation of the calcium hydroxide is increased to between 50 and 95% of maximum dissociation, preferably between 50 and 75% of maximum dissociation, more preferably between 75 and 95% of maximum dissociation, in some cases greater than 95% dissociation. By maximum dissociation is meant that when additional calcium hydroxide is added to the solution at a given temperature or pressure, the calcium hydroxide precipitates out regardless of the length of time or additional agitation. In some embodiments, agitation of the calcium hydroxide solution in a magnetic field increases the pH of the calcium hydroxide solution to at least one pH unit higher than a normal saturated $Ca(OH)_2$ solution, preferably up to about one point, and in certain embodiments as much as from about 1-3 points higher than a normal saturated $Ca(OH)_2$ solution. In further embodiments, agitating the solution in a strong magnetic field increases the solubility of the $Ca(OH)_2$ to greater than normal, preferably 2-200 times greater than normal, more preferably 50 to 100 times greater than normal, preferably 100 times greater than normal.

The magnetic field to which the calcium hydroxide solution is exposed may be generated by any means applicable. In some embodiments, the magnetic field may be generated by magnets, magnetic water treatment units or other magnetic field generating apparatus. Such magnetic field generating apparatus may be composed of one or a plurality of magnets which may surround, be placed around, or be otherwise disposed of adjacent to the container containing the $Ca(OH)_2$ solution. Any kind of magnet or apparatus that creates a strong magnetic field may be used. Magnets which may be used as part of magnetic water treatment units or to otherwise generate a magnetic field include, but are not limited to, NdFeB (Neodymium-Iron-Boron), Ferrite, AlNiCo (Aluminum-Nickel-Cobalt), SmCo (Samarium Cobalt), Alcomax (alloy of iron, nickel, aluminium, cobalt and copper), Cunife (copper, nickel and iron or copper, nickel, iron and cobalt), and Fernico (iron, nickle, cobalt) magnets. The magnets may be monopolar or bipolar. In other embodiments, the magnetic field generating apparatus may comprise electromagnets. In additional embodiments, the magnets may be encased in a housing. Such a housing may be made of any material applicable, including, but not limited to, metals such as, but not limited to, aluminum, or steel; and plastics, or any combination thereof. In some embodiments, magnets on opposing sides of the container holding the solution may have opposite poles, such that, for example, the positive and negative poles face each other. In other embodiments, the magnets may rotate around the container of calcium hydroxide solution.

In order to increase the $OH^-$ concentration of the calcium hydroxide solution, it may be combined with a solution made from sulfuric acid. In order to create the solution made from sulfuric acid, sulfuric acid is added to water. In some embodiments, enough sulfuric acid is added to water to create a solution of equal molar strength to the $Ca(OH)_2$ in the calcium hydroxide solution. In other embodiments, the concentration of the solution will be about 0.02% to about 0.08% acid in water by volume, preferably about 0.04% to about 0.06% acid in water by volume. In further embodiments the concentration may be about 50-100 ml of sulfuric acid (Baume 12°) per gallon of water, preferably about 70 to about 80 ml, more preferably about 70 to about 78 ml of sulfuric acid per gallon of water. In some embodiments, the sulfuric acid solution may be agitated until substantial dissociation occurs such that 75 to 100% of maximum dissociation is achieved, preferably 75 to 95% of maximum dissociation, more preferably 80 to 95% of maximum dissociation of sulfuric acid, in some instances greater than 95% dissociation of sulfuric acid.

In some embodiments, it may be desirable to reduce the acidity of the sulfuric acid solution. The reduction of acidity may occur through any means applicable. In some embodiments, the reduction of acidity may occur through the introduction of additional oxygen to the solution. In one embodiment, nascent oxygen may be introduced into the sulfuric acid solution. In another embodiment, the sulfuric acid solution may be treated with ozone by circulating the solution through ozone generators. The ozone generators dissociate an oxygen which is consumed by (2H+) ion(s) in the acid solution to create water. The acid solution may be re-circulated through the ozone units until a particular concentration of oxygen is absorbed or a particular pH is achieved. In some embodiments, the sulfuric acid solution will be run through the ozone generators until the pH increases by at least 1 point, in certain embodiments by at least 1-3 points, 1-4 points, and up to 1-6 points or more. In some embodiments, the sulfuric acid solution will be circulated through ozone generators until the pH reaches or exceeds about 7.0. The neutralized acid solution may then be slowly added to the calcium hydroxide solution to form a resultant mixture. The free calcium in the calcium hydroxide solution will react with the sulfate ions ($SO_4^{2-}$) in the acid solution to create insoluble anhydrous calcium sulfate precipitate. The mixture may then be agitated until the reaction goes to completion and the anhydrous calcium sulfate may be filtered or otherwise removed from the solution. In some embodiments, a non-ionic surfactant may be added to the resulting mixture in order to enhance precipitation. Such non-ionic surfactants may include, but are not limited to, linear or nonyl-phenol alcohols or fatty acids, alcohol ethoxylates, alkylphenol ethoxylates, alkyl polyglycosides, alkyl ethers such as polyoxyethylene octyl ether, polyoxyethylene lauryl ether, polyoxyethylene stearyl ether, and polyoxyethylene oleyl ether; alkyl phenyl ethers such as polyoxyethylene octylphenyl ether, and polyoxyethylene nonylphenyl ether; alkyl esters such as polyoxyethylene laurate, polyoxyethylene stearate, and polyoxyethylene oleate; alkylamines such as polyoxyethylene laurylamino ether, polyoxyethylene stearylamino ether, polyoxyethylene oleylamino ether, polyoxyethylene soybean amino ether, and polyoxyethylene beef tallow amino ether; alkylamides such as polyoxyethylene lauric amide, polyoxyethylene stearic amide, and polyoxyethylene oleic amide; vegetable oil ethers such as polyoxyethylene castor oil ether, and polyoxyethylene rapeseed oil ether; alkanolamides such as lauric acid diethanolamide, stearic acid diethanolamide, and oleic acid diethanolamide; and sorbitan ester ethers such as polyoxyethylene sorbitan monolaurate, polyoxyethylene sorbitan monopalmitate, polyoxyethylene sorbitan monostearate, and polyoxyethylene sorbitan monooleate.

In some embodiments, the solution may be filtered at various stages to remove particulates. For example, the calcium hydroxide solution may be filtered prior to combining with the sulfuric acid solution and/or the resultant mixture may be filtered to remove particulates. In other embodiments, the resultant mixture may be additionally cooled or partially frozen to create a slurry and further purified, for example through filtration. In one embodiment, the resulting mixture is cooled to below about 36° F. In another embodiment the resulting mixture is cooled to below about 36° F. but above about 35° F.

In some embodiments, the concentrated $OH^-$ solution prepared by combining the calcium hydroxide solution and sulfuric acid solution may be diluted with water to reach a specified pH prior to consumption or administration. In some embodiments, the water may be non-chlorinated. In other embodiments, the water may be spring water. In some embodiments, the resulting mixture may be diluted to a pH of between about 8.0 to about 11, more preferably between about 8.5 to about 9.5, more preferably between 8.5 to about 9.0. This solution may then be used to effectively neutralize acids, to treat acidosis, prophylactically, to reduce free radicals, and/or as an antioxidant.

The acid/alkaline balance in a healthy mammal is generally regulated through the actions of buffers, respiration and renal function. Two forms of acid are generated as a result of normal metabolic processes. Oxidative metabolism produces a large amount of $CO_2$ daily which is excreted through the lungs. The other form of acid results from the metabolism of dietary protein, resulting in the accumulation at an average rate of approximately 1 mmol per kilogram of body weight, or 50 to 70 mmol per day of acid in an average adult on a typical western meat containing diet.

The most important mechanism preventing change in the pH of extracellular fluid is the carbonic acid/bicarbonate buffer system. The importance of this buffer pair relates to certain key properties: bicarbonate is present in a relatively high concentration in the extracellular fluid (between 24 and 28 mmol/L) and the components of the buffer system are effectively under physiological control: the $CO_2$ by the lungs, and the bicarbonate by the kidneys. A shift in pH can be brought about by either a primary change in the bicarbonate concentration (metabolic disturbances) or in the partial pressure of $CO_2$ in the blood (respiratory disturbances).

Respiratory acidosis results from the accumulation of $CO_2$ in the body as a result of failure of pulmonary ventilation. This may occur from lesions either in the central nervous system (e.g. depression of cerebral function, spinal cord injury), in the peripheral nervous pathways involved in ventilating the lungs (peripheral nerve and muscle disorders), in some forms of lung disease involving impaired gas diffusion (e.g. emphysema, asthma, bronchitis, pneumonia, lung cancer or aspiration), or due to pharmaceutical causes.

Metabolic acidosis may result from inorganic acid addition, i.e. the infusion or ingestion of HCl or $NH_4Cl$; or through gastrointestinal base loss through conditions such as diarrhea, small bowel fistula/drainage, surgical diversion, and renal tubular disorders; stimulation of chemoreceptors; lactic acid accumulation; poison; or diet. The $OH^-$ solution of the present invention is effective in the treatment of acidosis regardless of cause.

Alkalinity increasing compositions of the invention typically comprise an amount of a base solution made from calcium hydroxide, its solvates, hydrates, or combinations thereof, which is effective for the treatment or prevention of acidosis, as well as complications and related conditions thereof in a mammalian subject. Typically, an alkalinity increasing effective amount of an $OH^-$ formulation will comprise an amount of the active compound which is therapeutically effective, in a single or multiple unit dosage form, over a specified period of therapeutic intervention, to measurably alleviate one or more symptoms of acidosis or related conditions in the subject. Within exemplary embodiments, these compositions are effective within in vivo treatment methods to alleviate acidosis. The active compound may be optionally formulated with a pharmaceutically acceptable carrier and/or various excipients, vehicles, stabilizers, buffers, preservatives, etc.

Oxidative metabolism may also cause oxidative stress. Oxidative stress is imposed on cells as a result of an increase in oxidant generation (including reactive oxygen species), a decrease in antioxidant protection, or a failure to repair oxidative damage. It is believed that intracellular and extracellular advanced glycation (AGEs) or lipoxidation end products (ALEs), together with dysregulated glucose and lipid metabolism, are important contributors to oxidant stress, enhanced cellular redox-sensitive transcription factor activity, and impaired innate immune defense, causing inappropriate inflammatory responses mediated in part by reactive oxygen species.

Oxygen has two unpaired electrons in separate orbitals in its outer shell. Sequential reduction of molecular oxygen leads to the formation of a group of reactive oxygen species including the superoxide anion, peroxide and hydroxyl radicals. Oxygen-derived radicals are generated constantly as part of normal aerobic life as oxygen is reduced along the electron transport chain in mitochondria. Reactive oxygen species are also formed as necessary intermediates in a variety of enzyme reactions.

However, these highly reactive radicals can also start a chain reaction which disrupts cellular function. While they are a natural byproduct of metabolic function as well as part of phagocytosis, an excess of free radicals can occur for a variety of reasons. For example, an increase in the production of free radicals can be produced by drugs such as antibiotics that depend on quinoid groups or bound metals for activity (nitrofurantoin), antineoplastic agents as bleomycin, anthracyclines (adriamycin) and methotrexate. In addition, radicals derived from penicillamine, phenylbutazone, some fenamic acids and the aminosalicylate component of sulphasalazine are currently believed to inactivate protease and deplete ascorbic acid accelerating lipid peroxidation. Free radical production may also be increased by radiation and smoking. Additionally, inhalation of inorganic particles also known as mineral dust (e.g. asbestos, quartz, and silica) can lead to lung injury due to free radical production. Fever, excess glucocorticoid therapy and hyperthyroidism also increase the generation of oxygen-derived radicals due to increased metabolism. Furthermore, a wide variety of environmental agents including photochemical air pollutants such as pesticides, solvents, anesthetics, exhaust fumes and aromatic hydrocarbons can cause free radical damage to cells.

Free radical and ROS damage can be inhibited by antioxidants. An antioxidant is a substance that when present in low concentrations relative to the oxidizable substrate significantly delays or reduces oxidation of the substrate. Antioxidants protect the body by reacting with free radicals and other reactive oxygen species within the body, hindering oxidation and reducing the amount of circulating free radicals. However, antioxidant supply is limited as an antioxidant molecule can only react with a single free radical. Therefore, there is a constant need to replenish antioxidant resources, whether endogenously or through supplementation. The compositions and methods of the present invention are effective as antioxidants for the elimination and/or reduction of reactive oxygen species including free radicals, regardless of the source of the free radicals.

Antioxidant compositions of the invention typically comprise an amount of a base solution made from calcium hydroxide, its solvates, hydrates, or combinations thereof, which is effective for the treatment or prevention of excess free radicals as well as complications and related conditions thereof in a mammalian subject. Typically, an antioxidant effective amount (or free radical reducing effective amount) of an OH$^-$ formulation of the present invention will comprise an amount of the active compound which is therapeutically effective, in a single or multiple unit dosage form, over a specified period of therapeutic intervention, to measurably alleviate one or more symptoms of free radical damage or related conditions in the subject. The active compound may be optionally formulated with a pharmaceutically acceptable carrier and/or various excipients, vehicles, stabilizers, buffers, preservatives, etc.

The amount, timing and mode of delivery of compositions of the invention comprising an effective amount of a base solution either as an alkalinity increasing agent, antioxidant agent, (or free radical reducing agent) or both will be routinely adjusted on an individual basis, depending on such factors as weight, age, gender, and condition of the individual, the severity of the acidosis and/or free radical damage or related symptoms, whether the administration is prophylactic or therapeutic, and on the basis of other factors known to effect drug delivery, absorption, pharmacokinetics, including, but not limited to, half-life, and efficacy.

An effective dose or multi-dose treatment regimen for the instant alkalinity increasing or antioxidant formulations will ordinarily be selected to approximate a minimal dosing regimen that is necessary and sufficient to substantially prevent or alleviate acidosis or excess free radicals and related conditions in the subject. A dosage and administration protocol will often include repeated dosing therapy over a course of several days or even one or more weeks or years. An effective treatment regime may also involve prophylactic dosage administered on a day or multi-dose per day basis lasting over the course of days, weeks, months or even years.

An "effective amount," "therapeutic amount," "therapeutic effective amount," or "effective dose" is an amount or dose sufficient to elicit a desired pharmacological or therapeutic effect in a mammalian subject; typically resulting in a measurable increase in alkalinity or reduction in free radicals.

Therapeutic efficacy can alternatively be demonstrated by a measurement of blood gases, electron spin resonance, spin trapping, fingerprinting, measurement of free radical markers, liquid chromatography, measurement of markers of oxidative stress, or by altering the nature, recurrence, or duration of symptoms associated with acidosis and/or excess free radicals including, but not limited to, gout, Lesch-Nyhan syndrome, hemochromatosis, Alzheimer's, amyotrophic lateral sclerosis, arthritis, atherosclerosis, cancer, cataracts, chronic gout, chronic obstructive pulmonary disease, diabetes, coronary artery disease, heart failure, hypertension, inflammatory bowel disease, macular degeneration, multiple sclerosis, Parkinson's, Reynaud's phenomenon, reperfusion injury, pancreatic impairment, respiratory disease, methicillin-resistant *Staphylococcus aureus*, hepatitis C, cellulitis, and infection. Therapeutic effectiveness may further be demonstrated by a reduction in the symptoms of skin conditions such as psoriasis, Morgellons disease and fungal infections such as candidiasis, tinea cruris, and tinea pedis. Therapeutic effectiveness may additionally be demonstrated by a reduction in the number of secondary infections experienced by a subject, particularly in a subject with a compromised immune system.

Therapeutic effectiveness may also be demonstrated by a decrease in the amount of other pharmaceutical agents necessary to treat a disease, or an increase in the effectiveness of current dosages. For example, the compositions of the present invention may increase the effectiveness of chemotherapeutic agents, decreasing the amount of chemotherapeutic agents needed or the length of the treatment needed.

Therapeutic effectiveness may be determined, for example, through an arterial blood gas. In an arterial blood gas test, arterial blood is taken from any easily accessible artery (typically either radial, brachial or femoral) or out of an arterial line. Once the sample is obtained, care should be taken to eliminate visible gas bubbles, as these bubbles can dissolve into the sample and cause inaccurate results. The sealed syringe is then taken to a blood gas monitor. The machine aspirates the blood from the syringe and measures the pH and the partial pressures of oxygen and carbon dioxide and the bicarbonate concentration, as well as the oxygen saturation of hemoglobin. Normal pH of blood is between about 7.4 and 7.3. Effective amounts of the mixtures of the present invention will increase plasma pH from below 7.0 to a pH of about 7.6 to 7.3. Effective alkalinity increasing amounts may increase plasma pH of 6.0 to a pH of about 6.5, preferably to about 6.7, more preferably to about 7.0, preferably to a pH of 7.4 or higher. Alkalinity increasing effectiveness may also be demonstrated by a 2-40%, 5-15%, 10-20% increase in the plasma pH.

Therapeutic effectiveness may also be demonstrated through a litmus test in which a sample of saliva is taken upon awakening and tested with a strip of litmus paper. A urine sample may also be tested with a strip of litmus paper or a litmus test strip. The litmus paper is then compared to a litmus scale to determine the pH of the sample. Optimally, the pH of saliva is about 7.4 and the pH of urine is about 6.6. The methods and compositions of the present invention are therapeutically effective to increase the pH of saliva and/or urine by about 2-40%, 5-15%, 10-20% or more.

Therapeutic effectiveness as a free radical scavenger may further be demonstrated through electron spin resonance. Electron spin resonance (ESR) is a spectroscopic technique which detects species that have unpaired electrons such as free radicals. The degeneracy of the electron spin states characterized by the quantum number, $m_S=\pm\frac{1}{2}$, is lifted by the application of a magnetic field and transitions between the spin levels are induced by radiation of the appropriate frequency. An un-paired electron interacts with its environment, and the details of ESR spectra depend on the nature of those interactions. The integrated intensity of the spectrum is proportional to the concentration of radicals in the sample. An effective free radical reducing or antioxidant amount of the mixture of the present invention will decrease the intensity of the spectrum by 2-50%, 10-40%, 15-30%, 20-25% or more.

Spin trapping provides a nitrone or nitrose compound for an addition reaction which produces an electron spin resonance spectroscopy-detectable aminoxyl radical. The product of the reaction can then be measured through electronic resonance spectroscopy. Effectiveness of the compositions of the present invention as a free radical scavenger may be demonstrated by a decrease in the product of the reaction by 2-50%, 10-40%, 15-30%, 20-25% or more.

Oxidative stress as a result of free radical production can be measured in myriad ways including, microplate cold light cytofluorimetry, and measurement of coiling of DNA, and cytochrome C production. Oxidative stress caused by free radicals may also be determined through measurement of thiobarbituric acid reacting substances, measurement of pentane and ethane, measurement of creatine kinase, and measurement of conjugated dienes. Effective free radical reducing or antioxidant amounts of the composition of the present invention will reduce the amount of the measured markers by 2-50%, 10-40%, 15-30%, 20-25% or more.

In microplate cold light cytofluoroimetry, permeable probes are inserted directly in living cells using a method of UV and visible fluorescent detection. Some particles are known to have fluorescence (such as cigarette smoke particles) when they react with free radicals and the amount of free radical damage can be assessed by the amount of fluorescence in a sample. A quantitative measure can be obtained using a flow cytometer. This method also evaluates intracellular glutathione and hydrogen peroxide production. A free radical reducing effective amount of a mixture of the present invention will decrease the fluorescence by 2-50%, 10-40%, 15-30%, 20-25% or more.

Therapeutic effectiveness of the solution as a free radical scavenger may further be demonstrated by the measurement of the proportion a relaxed coil DNA to that of supercoiled DNA wherein X=Relaxed coil DNA/Supercoiled DNA. Plasmid DNA is incubated with 5 µl of particle suspensions at 37° C. in a water bath. The supercoiled, relaxed coiled and linearised plasmid DNA are separated by electrophoresis and quantified by scanning. The higher the value of X, the more oxidative damage (based on free radicals damaging the supercoiled DNA and causing it to uncoil). An effective free radical reducing or antioxidant amount of a mixture of the present invention will decrease the value of X by 2-50%, 10-40%, 15-30%, 20-25% or more.

The rate of Cytochrome C reduction can be measured using luminol induced chemiluminescence for quantifying the results. Therapeutically effective free radical reducing or antioxidant amounts of the solution of the present invention will decrease the rate of cytochrome C reduction by 2-50%, 10-40%, 15-30%, 20-25% or more.

Following administration of the OH⁻ composition according to the formulations and methods of the invention, test subjects will exhibit a 5%, 10%, 20%, 30%, 50% or greater reduction, up to a 75-90%, or 95% or greater, reduction, in one or more symptoms associated with acidosis or excessive free radical production as compared to placebo-treated or other suitable control subjects. Test subjects may also exhibit a 10%, 20%, 30%, 50% or greater reduction, up to a 75-90%, or 95% or greater, reduction, in the symptoms of one or more conditions associated with acidosis or excessive free radical production including, but not limited to, gout, Lesch-Nyhan syndrome, hemochromatosis, Alzheimer's, amyotrophic lateral sclerosis, arthritis, atherosclerosis, cancer, cataracts, chronic gout, chronic obstructive pulmonary disease, diabetes, cellulitis, coronary artery disease, heart failure, hypertension, inflammatory bowel disease, macular degeneration, multiple sclerosis, Parkinson's, Reynaud's phenomenon, reperfusion injury, pancreatic impairment, infection, methicillin-resistant *Staphylococcus aureus*, secondary infections, hepatitis C and skin conditions such as psoriasis, Morgellons disease, candidiasis, tinea cruris, and tinea pedis.

The pharmaceutical compositions of the present invention may be administered by any means that achieves the intended therapeutic or prophylactic purpose. Suitable routes of administration for alkalizing and antioxidant compositions of the invention comprising OH⁻ solutions include, but are not limited to, oral, buccal, nasal, aerosol, mucosal, injectable, slow release, controlled release, iontophoresis, sonophoresis, and other conventional delivery routes, devices and methods. Injectable delivery methods are also contemplated, including but not limited to, intravenous, intramuscular, intraperitoneal, intraspinal, intrathecal, intracerebroventricular, intraarterial, and subcutaneous injection.

Within additional aspects of the invention, combinatorial formulations and coordinate administration methods are provided which employ an effective amount of OH⁻ compositions, and one or more additional active agent(s) that is/are combinatorially formulated or coordinately administered with the OH⁻ solution-yielding an effective formulation or method to modulate, alleviate, treat or prevent acidosis or excessive free radicals in a mammalian subject. Exemplary combinatorial formulations and coordinate treatment methods in this context employ a base solution in combination with one or more additional or adjunctive therapeutic agents.

Such additional or adjunctive therapeutic agents may be additional alkalinity increasing agents including, but not limited to sodium bicarbonate; a carbonate, a phosphate, or a hydroxide of sodium or potassium; magnesium carbonate; magnesium hydroxide; ammonium carbonate; ammonium bicarbonate; magnesium oxide; sodium or potassium citrate, bicarbonate, sulfate, and benzoate; ascorbate; calcium carbonate; or any pharmaceutically acceptable material that causes the pH of an aqueous medium to rise above pH 7.0, or mixtures thereof.

Additional or adjunctive therapeutic agents may also include antioxidants including, but not limited to, xanthine oxidase inhibitors, including, but not limited to, allopurinol and folic acid; NADPH oxidase inhibitors, including, but not limited to, adenosine; calcium channel blockers; superoxide dismutases; catalases; albumin; inhibitors of iron redox cycling, including, but not limited to deferoxamine, apotransferin and ceruloplasmin; beta carotene; ascorbates; myricetin-3-O-galactoside, quercitin-3-O-galactoside; and alpha tocopherol.

Additional or adjunctive therapeutic agents may also include compositions used to treat specific conditions such as gout, Lesch-Nyhan syndrome, hemochromatosis, Alzheimer's, amyotrophic lateral sclerosis, arthritis, atherosclerosis, cancer, cataracts, chronic gout, chronic obstructive pulmonary disease, diabetes, cellulitis, coronary artery disease, heart failure, hypertension, inflammatory bowel disease, macular degeneration, multiple sclerosis, Parkinson's, Reynaud's phenomenon, reperfusion injury, pancreatic impairment, infection, methicillin-resistant *Staphylococcus aureus*, hepatitis C and skin conditions such as psoriasis, Morgellons disease, candidiasis, tinea cruris, and tinea pedis. The use of these additional or adjunctive therapeutic agents in conjunction with the alkalizing or antioxidant agent of the present invention may increase the effectiveness of the therapeutic agents and/or decrease the amount of such agents that may be required.

In some embodiments, the alkalinity increasing agent may be administered in conjunction with an additional therapeutic agent to facilitate consumption of the additional therapeutic agent. For example, some therapeutic agents may be extremely acidic. Such agents may be administered in conjunction with the alkalinity increasing agent to neutralize the acidity and increase the forms of administration that would be acceptable. In another embodiment, the alkalinity increasing agent may be used to temporarily neutralize stomach acid or other acid conditions so that therapeutic agents which are destroyed by acid such as, but not limited to, nutritional supplements or other organics such as vitamins, including vitamin B12, can be ingested.

In certain embodiments, the invention provides combinatorial alkalizing or antioxidant formulations comprising a base solution made from calcium hydroxide and one or more adjunctive agent(s) having alkalizing or antioxidant activity, or both, or additional adjunctive agents which may have neither alkalizing nor antioxidant activity but which are useful in the treatment of underlying conditions or prophylactically. Within such combinatorial formulations, the $OH^-$ solution and the adjunctive agent(s) having alkalizing and/or antioxidant activity, or non-alkalizing/antioxidant agents will be present in a combined formulation in effective amounts, alone or in combination. In exemplary embodiments, a base solution and a non-calcium hydroxide based alkalizing and/or antioxidant agent will each be present in an alkalizing and/or antioxidant amount (i.e., in singular dosage which will alone elicit a detectable alkalizing or free radical reduced response in the subject). Alternatively, the combinatorial formulation may comprise one or both of the $OH^-$ solution and a non-calcium hydroxide based alkalizing and/or antioxidant agent or other adjunctive agent in sub-therapeutic singular dosage amount(s), wherein the combinatorial formulation comprising both agents features a combined dosage of both agents that is collectively effective. Effectiveness may elicit an alkalizing or free radical reducing response or other increased therapeutic response. Thus, one or both of the $OH^-$ solution and a non-calcium hydroxide based alkalizing and/or antioxidant agents may be present in the formulation, or administered in a coordinate administration protocol, at a sub-therapeutic dose, but collectively in the formulation or method they elicit a detectable alkalizing and/or antioxidant response in the subject.

To practice the coordinate administration methods of the invention, an $OH^-$ mixture is administered, simultaneously or sequentially, in a coordinate treatment protocol with one or more of the secondary or adjunctive therapeutic agents contemplated herein. The coordinate administration may be done simultaneously or sequentially in either order, and there may be a time period while only one or both (or all) active therapeutic agents, individually and/or collectively, exert their biological activities. A distinguishing aspect of all such coordinate treatment methods is that the $OH^-$ solution exerts at least some detectable alkalizing or antioxidant activity, and/or elicits a favorable clinical response, which may or may not be in conjunction with a secondary clinical response provided by the secondary therapeutic agent. Often the coordinate administration of a base solution with a secondary therapeutic agent as contemplated herein will yield an enhanced therapeutic response beyond the therapeutic response elicited by either or both the $OH^-$ solution and/or secondary therapeutic agent alone.

The amount, timing and mode of delivery of compositions of the invention comprising an effective amount of a base solution of the present invention will be routinely adjusted on an individual basis, depending on such factors as weight, age, gender, and condition of the individual, the severity of the acidosis, ROS levels including free radical production or related symptoms, whether the administration is prophylactic or therapeutic, and on the basis of other factors known to effect drug delivery, absorption, pharmacokinetics, including, but not limited to, half-life, and efficacy.

Effective doses may be extrapolated from dose-response curves derived from in vitro or animal model test systems. Such animal models and systems are well known in the art. The precise dose to be employed will also depend on the route of administration, the seriousness of the disease or disorder, and body size, and should be decided according to the judgment of the practitioner and each patient's circumstances. However, suitable dosage ranges for oral administration are generally about 20 to about 75 ounces of the diluted $OH^-$ solution (having a pH between 8.0 and 9.5) per day. In specific preferred embodiments of the invention, the oral dose is about 24 to about 60 ounces of $OH^-$ solution per day, more preferably about 24 to about 45 ounces of $OH^-$ solution per day, more preferably about 24 to about 32 ounces per day, more preferably about 32 to about 48 ounces per day, more preferably about 35 to about 60 ounces per day. In some embodiments, the $OH^-$ solution is administered over the course of a day, for example the dosage is taken over eight hours, ten hours, twelve hours or 24 hours. In other embodiments, fractions of the dosage are administered at particular time points, for example every hour, every two hours, every three hours, every four hours, every eight hours, every twelve hours, or any other fraction of time, as tolerated by the patient. The dosage amounts described herein refer to total amounts administered; that is, if the $OH^-$ solution administered, the preferred dosages correspond to the total amount administered. Oral compositions preferably contain about 10% to about 95% active ingredient by weight. In one embodiment, one ounce of anti-oxidant material could be mixed in 1 liter of water. In another embodiment, three ounces of anti-oxidant material would be mixed in two liters of water. In a further embodiment, once the desired physiological pH level is obtained, a maintenance dose may be taken indefinitely. In some embodiments, a maintenance dose may be ½ of the therapeutic level, ⅓ of the therapeutic level, ¼ of the therapeutic level, or any other reduced dosage as determined by the judgment of the practitioner and the patient's circumstances.

The formulations may be presented in unit-dose or multi-dose containers. Preferred unit dosage formulations are those containing a daily dose or unit, daily sub-dose, as described herein above, or an appropriate fraction thereof, of the active ingredient(s). In one embodiment eight ounces of the prepared formulation is administered every four hours. In another embodiment, eight ounces of the prepared formulation is administered every three hours. In still another embodiment, eight ounces of the prepared formulation is administered every two hours or fraction thereof.

Pharmaceutical dosage forms of the $OH^-$ solution of the present invention include excipients recognized in the art of pharmaceutical compounding as being suitable for the preparation of dosage units as discussed above. Such excipients include, without intended limitation, binders, fillers, lubricants, emulsifiers, suspending agents, sweeteners, flavorings, preservatives, buffers, and other conventional excipients and additives.

The compositions of the invention for altering physiological pH can thus include any one or combination of the following: a pharmaceutically acceptable carrier or excipient; other medicinal agent(s); pharmaceutical agent(s); adjuvants; buffers; preservatives; diluents; and various other pharmaceutical additives and agents known to those skilled in the art. These additional formulation additives and agents will often be biologically inactive and can be administered to patients without causing deleterious side effects or interactions with the active agent.

Additional $OH^-$ solutions of the invention can be prepared and administered in any of a variety of inhalation or nasal delivery forms known in the art. Devices capable of depositing aerosolized $OH^-$ formulations in the sinus cavity or pulmonary alveoli of a patient include metered dose inhalers, nebulizers, sprayers, and the like. Methods and compositions suitable for pulmonary delivery of drugs for systemic effect are well known in the art. Suitable formulations, wherein the carrier is a liquid, for administration, as for example, a nasal spray or as nasal drops, may include aqueous or oily solutions of calcium hydroxide and any additional active or inactive ingredient(s).

Yet additional $OH^-$ formulations are provided for parenteral administration, including aqueous and non-aqueous sterile injection solutions which may optionally contain antioxidants, buffers, bacteriostats and/or solutes which render the formulation isotonic with the blood of the mammalian subject; and aqueous and non-aqueous sterile suspensions which may include suspending agents and/or thickening agents.

In more detailed embodiments, $OH^-$ compositions may be encapsulated for delivery in microcapsules, microparticles, or microspheres, prepared, for example, by coacervation techniques or by interfacial polymerization, in colloidal drug delivery systems (for example, liposomes, albumin microspheres, microemulsions, nano-particles and nanocapsules) or in macroemulsions.

In further embodiments, the pharmaceutical agents of the invention may be administered parenterally, e.g. intravenously, intramuscularly, subcutaneously or intraperitoneally. The parenteral preparations may be solutions, dispersions or emulsions suitable for such administration. The subject agents may also be formulated into polymers for extended release following parenteral administration. Pharmaceutically acceptable formulations and ingredients will typically be sterile or readily sterilizable, biologically inert, and easily administered. Such polymeric materials are well known to those of ordinary skill in the pharmaceutical compounding arts.

The invention disclosed herein will also be understood to encompass methods and compositions comprising a base solution using in vivo metabolic products of the said compounds (either generated in vivo after administration of the subject precursor compound, or directly administered in the form of the metabolic product itself). Such products may result, for example, from the oxidation, reduction, hydrolysis, amidation, esterification and the like of the administered compound, primarily due to enzymatic processes. Accordingly, the invention includes methods and compositions of the invention employing compounds produced by a process comprising contacting a base solution of the present invention with a mammalian subject for a period of time sufficient to yield a metabolic product thereof.

The above disclosure generally describes the present invention. A more complete understanding can be obtained by referring to the following examples. These examples are described solely for purposes of illustration and are not intended to limit the scope of the invention. Although specific terms have been employed herein, such terms are intended for descriptive use and not for purposes of limitation.

EXAMPLES

As demonstrated in the examples below, the present invention relates to the creation of a strong base solution for use as an antioxidant and/or alkalinity increasing agent.

Example I

Preparation of Basic Solution 50,000 g of $Ca(OH)_2$ is added to 500 gallons of water (100 g/gal) in a polyurethane tank surrounded by strong monopolar magnets. The mixture is stirred until maximum disassociation is achieved. The solution is then passed through a 10 micron filter to remove any particulates. 78 ml of concentrated sulfuric acid (Baume 12°) per gallon, (39000 ml total) is added to a second polyurethane tank containing 500 gallons of pure water. The acid solution is circulated through an OzoTech OZ2PCS ozone generator (OzoTech, Inc., Yreka, Calif.) until the pH of the solution is above 7.0. The diluted sulfuric acid is then added to the filtered $Ca(OH)_2$ solution and the reaction is allowed to go to completion. The resulting solution is passed through a 10 micron filter to remove any anhydrous calcium sulfate.

Example II

Additional Purification of $Ca(OH)_2$ Solution

The solution of example I is chilled to below 36° F. for up to four hours, but not allowed to freeze completely. The partially frozen material is then filtered using a 6 micron filter to remove any newly precipitated anhydrous calcium sulfate and/or ice. This increases the negative charge and the molar strength of the solution.

Example III

Preparation of an Antioxidant Solution

The solution of example I is added to non-chlorinated drinking water until a pH of 8.5 to 9.0 is achieved.

Example IV

Treatment for Increasing Physiological pH

The solution of Example III was administered at the rate of 8 ounces every four hours until 24 to 32 ounces of the solution was consumed. Consumption of this amount increases physiological pH to normal levels and decreases rates of infection.

Example V

Treatment of Fungal Infections

Solutions of the basic solution of Example I, diluted to a pH of 11, were applied topically once a day to areas of tinea infection. The solution controlled the infection and prevented it from spreading.

Example VI

Preparation and Use of an Antioxidant Solution

An alcohol extraction of Dwarf Mistletoe, *Arceuthobium campyopodum*, was prepared to extract myricetin-3-O-galactoside and quercitin-3-O-galactoside. The berries of the Dwarf Mistletoe were harvested and then ground into a coarse powder. The powder was then placed in an Erlenmeyer flask with 80% cold methanol. After 24 hours, the methanol was decanted and saved, and a second aqueous extraction was carried out for a further 24 hours. The combined methanol eluents were evaporated under vacuum leaving an aqueous solution. A half ounce of the aqueous solution was then combined with 1 liter of the solution of Example I which had been diluted to a pH of 11. The resulting solution may then be taken over 8 hours.

Although the foregoing invention has been described in detail by way of example for purposes of clarity of understanding, it will be apparent to the artisan that certain changes and modifications may be practiced within the scope of the appended claims which are presented by way of illustration not limitation. In this context, various publications and other references have been cited with the foregoing disclosure for economy of description. Each of these references is incorporated herein by reference in its entirety for all purposes. It is noted, however, that the various publications discussed herein are incorporated solely for their disclosure prior to the filing date of the present application, and the inventors reserve the right to antedate such disclosure by virtue of prior invention.

We claim:

1. A method for preparing a resultant mixture having a high concentration of OH− ions comprising:
    a) preparing a first solution by adding calcium hydroxide to water;
    b) agitating the first solution in a magnetic field to increase a rate or amount of dissociation of the calcium hydroxide;
    c) preparing a second solution by adding sulfuric acid to water to produce a sulfuric acid solution;
    d) agitating the second solution to increase a rate or amount of dissociation subjecting the second solution to ozone treatment to reduce the acidity of the sulfuric acid solution; and
    e) combining the first and second solution to produce a resultant mixture.

2. A method of increasing alkalinity in a vertebrate subject suffering from acidosis comprising:
    a) preparing a first solution by adding calcium hydroxide to water;
    b) agitating the first solution in a magnetic field to increase a rate or amount of dissociation of the calcium hydroxide;
    c) preparing a second solution by adding sulfuric acid to water to produce a sulfuric acid solution;
    d) agitating the second solution to increase a rate or amount of dissociation of sulfuric acid;
    e) subjecting the second solution to ozone treatment to reduce the acidity of the sulfuric acid solution;
    f) combining the first and second solution to produce a resultant mixture;
    g) diluting the resultant mixture in water to a pH of about 8.5 to about 9.5 to create a diluted resultant mixture; and
    h) administering an alkalinity increasing amount of the diluted resultant mixture to the vertebrate subject.

3. The method of claim 2, wherein the molarity of the sulfuric acid in the second solution is equal to the molarity of the calcium hydroxide in the first solution.

4. The method of claim 2, wherein agitating the calcium hydroxide solution in a magnetic field increases the dissociation of the calcium hydroxide to 75-95% of a maximal dissociation of calcium hydroxide.

5. The method of claim 2, wherein the magnetic field is generated by magnets.

6. The method of claim 5, wherein the magnets are monopolar.

7. The method of claim 2, wherein agitating the second solution increases the dissociation of sulfuric acid to 75 to 95% of a maximal dissociation of sulfuric acid.

8. The method of claim 2, wherein agitating the calcium hydroxide in the magnetic field increases the pH of the first solution at least one pH unit higher than a normal saturated $Ca(OH)_2$ solution.

9. The method of claim 2, wherein agitating the calcium hydroxide in the magnetic field increases the solubility of $Ca(OH)_2$ from about 2 to about 200 times greater than normal.

10. The method of claim 2, wherein the second solution is treated with ozone until the pH of the second solution is at least 7.0.

11. The method of claim 2, wherein the vertebrate is a mammal.

12. The method of claim 2, further comprising administering an antioxidant selected from a xanthine oxidase inhibitor, NADPH oxidase inhibitor, a calcium channel blocker, a superoxide dismutase, a catalase, albumin, an inhibitor of iron redox cycling, beta carotene, ascorbate, myricetin-3-O-galactoside, quercitin-3-O-galactoside, or alpha tocopherol to the vertebrate subject.

13. The method of claim 2, wherein the alkalinity increasing amount comprises between about 20 to about 75 ounces of the composition per day.

14. The method of claim 2, wherein the alkalinity increasing effective amount comprises about 8 ounces every four hours.

15. The method of claim 2, further comprising administering an additional alkalinity increasing agent to the vertebrate subject.

* * * * *

UNITED STATES PATENT AND TRADEMARK OFFICE
CERTIFICATE OF CORRECTION

PATENT NO. : 8,273,384 B2
APPLICATION NO. : 12/167123
DATED : September 25, 2012
INVENTOR(S) : Stephen Ray Wurzburger It is certified that error appears in the above-identified patent and that said Letters Patent is hereby corrected as shown below:

On the cover page, at (76), the last name of the inventor should be corrected to "Wurzburger".

Signed and Sealed this
Fifth Day of March, 2013

Teresa Stanek Rea
*Acting Director of the United States Patent and Trademark Office*